US009521953B2

(12) United States Patent
Toida

(10) Patent No.: US 9,521,953 B2
(45) Date of Patent: Dec. 20, 2016

(54) MEASUREMENT DEVICE AND MEASUREMENT METHOD

(71) Applicant: SAITAMA MEDICAL UNIVERSITY, Saitama (JP)

(72) Inventor: Masahiro Toida, Kawasaki (JP)

(73) Assignee: Saitama Medical University (JP)

(*) Notice: Subject to any disclaimer, the term of this patent is extended or adjusted under 35 U.S.C. 154(b) by 324 days.

(21) Appl. No.: 14/381,021

(22) PCT Filed: Feb. 26, 2013

(86) PCT No.: PCT/JP2013/054992
§ 371 (c)(1),
(2) Date: Aug. 26, 2014

(87) PCT Pub. No.: WO2013/129412
PCT Pub. Date: Sep. 6, 2013

(65) Prior Publication Data
US 2015/0005641 A1   Jan. 1, 2015

(30) Foreign Application Priority Data

Feb. 27, 2012  (JP) ................ 2012-039854

(51) Int. Cl.
A61B 5/00       (2006.01)
G01N 21/65      (2006.01)
(Continued)

(52) U.S. Cl.
CPC .......... A61B 5/0075 (2013.01); A61B 5/0066 (2013.01); G01B 9/02029 (2013.01);
(Continued)

(58) Field of Classification Search
CPC . A61B 5/0075; A61B 5/0066; G01N 21/4795; G01N 21/65; G01N 33/50; G01N 2201/06113; G01N 2201/0697; G01B 9/02029; G01B 9/02091
See application file for complete search history.

(56) References Cited

U.S. PATENT DOCUMENTS 5,275,168 A * 1/1994 Reintjes ............ G01N 21/4795
                                                     356/301
2005/0280827 A1* 12/2005 Potma .................... G01J 3/44
                                                     356/485
(Continued)

FOREIGN PATENT DOCUMENTS

JP   H07-294435 A   11/1995
JP   2007-101249 A   4/2007
(Continued)

OTHER PUBLICATIONS

Extended European Search Report for EP 13 75 4442 dated Oct. 5, 2015 (7 pages).
(Continued)

Primary Examiner — Peter Luong
(74) Attorney, Agent, or Firm — Harness, Dickey & Pierce, P.L.C.

(57) ABSTRACT

A measurement device includes: a light source that generates a pump beam and a Stokes beam; a pulse stretch section that stretches the pulse of the pump beam so that the pulse width of the Stokes beam is shorter than the pulse width of the pump beam; an optical splitter that splits the Stokes beam into two beams; an optical scan section that scans a subject with the pulse-stretched pump beam and one of the two beams split by the optical splitter; a first optical detector that detects an anti-Stokes beam from the subject; a second optical detector that detects an interference beam of the other of the two beams and the Stokes beam reflected by the subject; and a signal processing section that performs an image generation process based on a detection signal from the first optical detector and a detection signal from the second optical detector.

12 Claims, 5 Drawing Sheets

(51) Int. Cl.
*G01B 9/02* (2006.01)
*G01N 33/50* (2006.01)
*G01N 21/47* (2006.01)

(52) U.S. Cl.
CPC ..... *G01B 9/02091* (2013.01); *G01N 21/4795* (2013.01); *G01N 21/65* (2013.01); *G01N 33/50* (2013.01); G01N 2021/653 (2013.01); G01N 2201/0697 (2013.01); G01N 2201/06113 (2013.01)

(56) References Cited

U.S. PATENT DOCUMENTS

| | | |
|---|---|---|
| 2006/0192969 A1 | 8/2006 | Marks et al. |
| 2007/0076211 A1 | 4/2007 | Toida et al. |
| 2007/0088219 A1 | 4/2007 | Xie et al. |
| 2008/0304074 A1 | 12/2008 | Brennan, III |
| 2010/0177307 A1 | 7/2010 | Rimke et al. |

FOREIGN PATENT DOCUMENTS

| | | |
|---|---|---|
| JP | 2009-511175 A | 3/2009 |
| JP | 2010-145270 A | 7/2010 |
| JP | 2010-529465 A | 8/2010 |
| WO | WO-2013-047698 A1 | 4/2013 |

OTHER PUBLICATIONS

Masahiro Toida, "Coherent Anti-Stokes Raman Scattering ni yoru Mushinshu Kettochi Monitor no Kenkyu", Journal of Saitama Medical University, Aug. 2012, vol. 39, No. 1, pp. 19 to 23. (English Translation not available).

* cited by examiner

MEASUREMENT DEVICE AND MEASUREMENT METHOD

CROSS-REFERENCE TO RELATED APPLICATIONS

This application is a U.S. National Stage Application of International Application No. PCT/JP2013/054992 filed on Feb. 26, 2013, and published in Japanese as WO 2013/129412 A1 on Sep. 6, 2013. This application claims priority to Japanese Application No. 2012-039854 filed on Feb. 27, 2012. The entire disclosures of the above applications are incorporated herein by reference.

TECHNICAL FIELD

The present invention relates to a measurement device and a measurement method that measures structural information and molecular information about a subject.

BACKGROUND ART

Light is highly adaptive physical energy for performing non-invasive in vivo measurement. However, three problems (see below) specific to a living body occur when performing in vivo optical measurement. The first problem is a scattering phenomenon. Specifically, since light that has undergone scatter transmission or scatter reflection holds propagation historical information and position information to only a small extent, it is very difficult to implement quantitative determination and visualization. The second problem is interference due to intrinsic substances. Spectroscopic measurement is useful for identifying a specific biomolecule. However, intrinsic substances include various fluorescent substances that absorb ultraviolet light and visible light, and may result in an artifact. Therefore, it is difficult to distinguish a signal specific to the target substance. The third problem is a wavelength mismatch. A biomolecule can be specified by vibrational absorption (e.g., C—C, C—H, and C—O). The vibrational absorption wavelength band is the infrared region. A living body has a water content of about 60%. Absorption by water is high in the infrared region, and hinders vibrational spectroscopic measurement on a deep area of tissue. Tissue has high transmittance in a wavelength band of 0.7 to 1.2 micrometers. This wavelength band is referred to as "biological optical window". As described above, the optical characteristics of the measurement target and the probe wavelength mismatch make it difficult to acquire the biological information when performing in vivo optical measurement.

A contribution of advanced technology to health and medicine in the future can be easily determined based on disease progression and the current technology. A disease develops due to genetic alteration, and progresses through expression of abnormal proteins, a functional change and a structural change in cells and tissue, and development of a subjective symptom. On the other hand, diagnostic technology has been developed to go back through disease progression. Specifically, diagnostic technology has been developed from determination of symptoms based on a doctor's five senses and experience to imaging diagnostic technology that determines a structural change in an early stage.

In recent years, it has become possible to genetically determine the risk of diseases along with significant development of genetic diagnosis technology. However, it is difficult to determine the development timing of a disease. In view of the above situation, it is important to accurately determine the development of a disease in an early stage, and implement less invasive treatment in the future. It is important to determine a functional change that occurs prior to a structural change in order to find a disease in an early stage. Specifically, it is desired to implement molecular imaging of a specific protein in cells and tissue while maintaining the tissue structure that maintains homeostasis.

A molecular imaging method that utilizes light is classified into a probe method that utilizes a fluorescent labeling reagent or the like, and a non-probe method that utilizes the characteristics of an intrinsic substance. Coherent anti-Stokes Raman scattering (CARS) imaging has been known as a non-probe method that solves the above wavelength mismatch (see JP-A-7-294435, for example). However, since the distribution of the measurement target molecules lacks spatial characteristics, the molecular imaging resolution is normally low. Detailed spatial position information about the target molecules is indispensable for clarifying the onset mechanism and the progression mechanism of various diseases. Specifically, it is important to develop molecular imaging based on structural information.

Optical coherence tomography (OCT) has been known as a non-invasive in vivo structural imaging technique. In recent years, in vivo cell imaging that utilizes a broad-band light source using a short-pulse laser beam has been reported. Spectral OCT that extracts spectral information about a sample utilizing the broad-band characteristics of a light source has also been proposed. An OCT signal reflects absorption and scatter due to a sample, and it is possible to extract the spectral information to a certain extent when using a low-scattering sample. However, an error increases when using a scattering body such as tissue, and it is difficult to acquire the spectral information sufficient to identify a substance.

SUMMARY OF THE INVENTION

Technical Problem

It has been desired to simultaneously measure the structural information and the molecular information when implementing non-invasive in vivo measurement on a biological sample (solid, organ, and tissue).

The invention was conceived in view of the above technical problem. An object of the invention is to provide a measurement device and a measurement method that can simultaneously measure the structural information and the molecular information about the subject.

Solution to Problem (1) According to one aspect of the invention, there is provided a measurement device including:

a light source section that generates a pump beam and a Stokes beam that are applied to a subject;

a pulse stretch section that stretches a pulse of the pump beam so that a pulse width of the Stokes beam is shorter than a pulse width of the pump beam;

an optical splitter section that splits the Stokes beam into two beams;

an optical scan section that scans the subject with the pulse-stretched pump beam and one of the two beams split by the optical splitter section;

a first optical detection section that detects an anti-Stokes beam from the subject, and outputs a detection signal;

a second optical detection section that detects an interference beam of the other of the two beams split by the optical splitter section and the Stokes beam reflected by the subject, and outputs a detection signal; and a signal processing section that performs an image generation process based on the detection signal from the first optical detection section and the detection signal from the second optical detection section.

According to another aspect of the invention, there is provided a measurement method including:

a light source process that generates a pump beam and a Stokes beam that are applied to a subject;

a pulse stretch process that stretches a pulse of the pump beam so that a pulse width of the Stokes beam is shorter than a pulse width of the pump beam;

an optical split process that splits the Stokes beam into two beams;

an optical scan process that scans the subject with the pulse-stretched pump beam and one of the two beams split by the optical split process;

a first optical detection process that detects an anti-Stokes beam from the subject, and outputs a detection signal;

a second optical detection process that detects an interference beam of the other of the two beams split by the optical split process and the Stokes beam reflected by the subject, and outputs a detection signal; and a signal processing process that performs an image generation process based on the detection signal output by the first optical detection process and the detection signal output by the second optical detection process.

According to the aspects of the invention, the S/N ratio of the anti-Stokes beam (CARS beam) detection signal can be improved by stretching the pulse of the pump beam so that the pulse width of the Stokes beam is shorter than the pulse width of the pump beam. It is also possible to avoid a mismatch in optical pulse when combining CARS and OCT by utilizing the Stokes beam as the OCT measurement beam. This makes it possible to combine CARS and OCT, and simultaneously measure the molecular information and the structural information about the subject.

(2) In the measurement device and the measurement method, the pulse-stretched pump beam may be a picosecond pulse laser beam, and the Stokes beam may be a femtosecond pulse laser beam.

It is possible to improve the S/N ratio of the anti-Stokes beam (CARS beam) detection signal, and avoid a mismatch in optical pulse when combining CARS and OCT by utilizing a picosecond pulse laser beam as the pump beam, and utilizing a femtosecond pulse laser beam as the Stokes beam (OCT measurement beam). This makes it possible to combine CARS and OCT, and simultaneously measure the molecular information and the structural information about the subject.

(3) In the measurement device, the light source section may include an optical parametric oscillator that utilizes a second harmonic of the pump beam as an excitation beam, and generate an idler beam of the optical parametric oscillator as the Stokes beam.

In the measurement method, the light generation process may generate an idler beam of an optical parametric oscillator as the Stokes beam, the optical parametric oscillator utilizing a second harmonic of the pump beam as an excitation beam.

(4) The measurement device may further include an optical modulation section that modulates a wavelength of a signal beam from the optical parametric oscillator, and the first optical detection section may detect an interference beam of the wavelength-modulated signal beam and the anti-Stokes beam from the subject, and output the detection signal.

The measurement method may further include an optical modulation process that modulates a wavelength of a signal beam from the optical parametric oscillator, and the first optical detection process may detect an interference beam of the wavelength-modulated signal beam and the anti-Stokes beam from the subject, and output the detection signal.

It is possible to detect the anti-Stokes beam (CARS beam) signal with high sensitivity by performing heterodyne detection using the signal beam of the optical parametric oscillator as the reference beam.

DESCRIPTION OF EMBODIMENTS

Exemplary embodiments of the invention are described below. Note that the following exemplary embodiments do not unduly limit the scope of the invention as stated in the claims. Note also that all of the elements described below in connection with the exemplary embodiments should not necessarily be taken as essential elements of the invention.

The measurement principle of a measurement device and a measurement method according to several embodiments of the invention is described below.

The measurement device and the measurement method according to several embodiments of the invention make it possible to combine optical coherence tomography (OCT) that implements excellent structural imaging even under light scattering conditions, and coherent anti-Stokes Raman scattering (CARS) that implements molecular imaging by discriminating in vivo molecules via vibrational spectroscopy, when implementing non-invasive in vivo imaging on a biological sample (solid, organ, and tissue).

Since OCT and CARS differ to a large extent as to the optimum optical pulse width during measurement, it is impossible to simply combine OCT and CARS. CARS is characterized in that the molecular signal vibration S/N ratio is limited by a non-resonance signal, and utilizes a pump beam and a Stokes beam having a pulse width of several to several tens of picoseconds in order to ensure a sufficient resonance signal/non-resonance signal ratio and a sufficient spectral resolution (several $cm^{-1}$). On the other hand, OCT utilizes an ultrashort pulse having a pulse width of several tens to several hundreds of femtoseconds (spectral width=about 1000 $cm^{-1}$) in order to implement high-resolution structural imaging. Specifically, it is necessary to deal with the mismatch in optical pulse when combining OCT and CARS.

Figure 1:
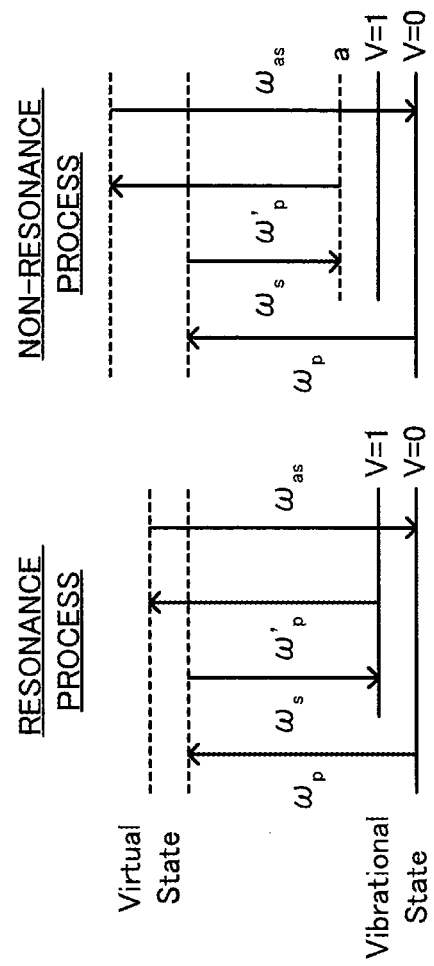
FIG. 1 is a view illustrating the energy relationship between photons and molecular vibrations when implementing CARS.

FIG. 1 illustrates the energy relationship between photons and molecular vibrations when implementing CARS. A CARS signal is classified into a signal based on a resonance process in which relaxation of molecular vibrations to the V=0 level through the V=1 level occurs via generation of an anti-Stokes beam $\omega_{as}$, and a non-resonance process in which relaxation of molecular vibrations to the V=0 level through the virtual level a occurs via generation of the anti-Stokes beam $\omega_{as}$. It is indispensable to synchronize the pump beam and the Stokes beam (i.e., apply the pump beam pulse and the Stokes beam pulse to the subject at the same time) during the non-resonance process since relaxation occurs without through the V=1 level (i.e., through the virtual level a). However, since the molecules excited to the V=1 level through mixing of the pump beam $\omega_p$ and the Stokes beam $\omega_s$ in the initial stage is further excited by the pump beam $\omega'_p$ in the subsequent stage during the resonance process, it suffices to use only the pump beam $\omega'_p$ (i.e., it is unnecessary to use the Stokes beam $\omega_s$) for excitation in the subsequent stage.

The measurement device and the measurement method according to several embodiments of the invention focus on the characteristics of the resonance process and the non-resonance process during CARS, improve the CARS signal resonance process/non-resonance process ratio, and avoid a mismatch in optical pulse when combining CARS and OCT by utilizing the Stokes beam $\omega_s$ during the initial-stage excitation process as an OCT measurement beam. The measurement device and the measurement method thus make it possible to combine CARS and OCT.

First Embodiment

Figure 2:
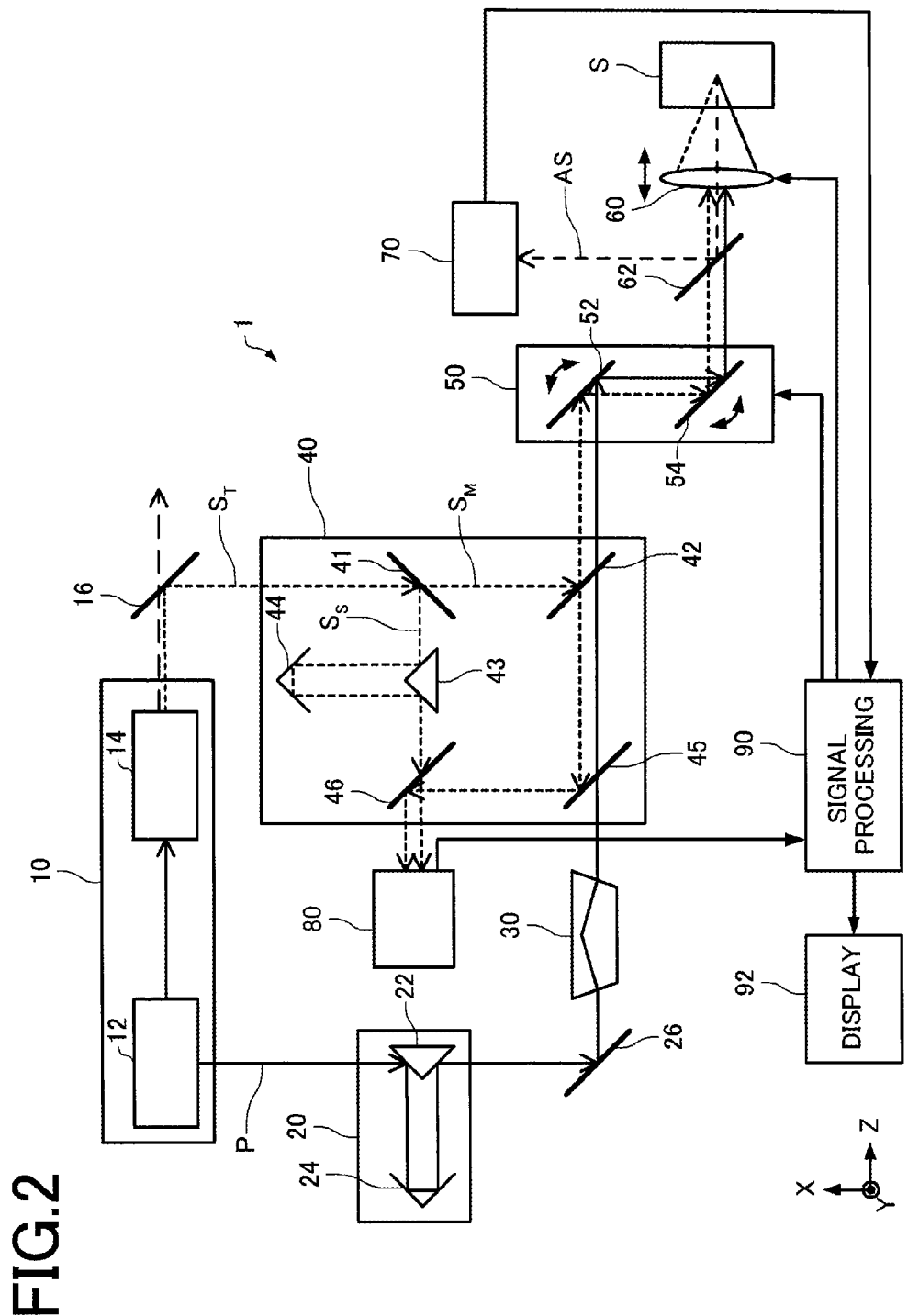
FIG. 2 is a view illustrating an example of the configuration of a measurement device according to a first embodiment.

FIG. 2 illustrates an example of the configuration of a measurement device according to a first embodiment. A measurement device 1 includes a light source section 10 that generates a pump beam and a Stokes beam that are applied to a subject (sample) S, an optical delay section 20 that adjusts the timing at which the pump beam and the Stokes beam are applied to the subject S, a pulse stretch section 30 that stretches the pulse width of the pump beam so that the pulse width of the Stokes beam is shorter than the pulse width of the pump beam, an optical interference section 40 that causes the Stokes beam (OCT reference beam) to interfere with the Stokes beam reflected by the subject S, an optical scan section 50 that scans the subject S with the pump beam and the Stokes beam, an objective lens 60 that condenses the pump beam and the Stokes beam on the subject S, a first optical detection section 70 that detects an anti-Stokes beam (CARS beam) from the subject S, a second optical detection section 80 that detects an interference beam of the Stokes beam (OCT reference beam) and the Stokes beam reflected by the subject S, a signal processing section 90, and a display section 92.

The light source section 10 includes a laser light source 12 that generates a femtosecond-pulse fundamental wave and a second harmonic, and an optical parametric oscillator (OPO) 14 that utilizes the second harmonic as an excitation beam. The laser light source 12 may be implemented by a Yb:YAG laser crystal, for example. The Yb:YAG laser generates a fundamental wave having a wavelength of 1034 nm, and a second harmonic having a wavelength of 517 nm. The fundamental wave from the laser light source 12 is extracted as a pump beam pulse, and an idler beam from the optical parametric oscillator 14 is extracted as a Stokes beam pulse. The angle of the crystal axis of the optical parametric oscillator 14 is adjusted so that the difference between the angular frequency $\omega_p$ of the fundamental wave (pump beam) and the angular frequency $\omega_s$ of the idler beam (Stokes beam) is equal to the vibrational frequency $\omega_\gamma$ of the measurement target molecule (i.e., $(\omega_\gamma = \omega_p - \omega_s)$).

The pump beam P from the light source section 10 is delayed by the optical delay section 20 that includes two mirrors 22 and 24, and enters the pulse stretch section 30 through a mirror 26. The pulse stretch section 30 is formed of an optical material that has negative or positive refractive index dispersion characteristics, for example. The pulse stretch section 30 stretches the pulse width of the pump beam P. The pump beam P of which the pulse width has been stretched by the pulse stretch section 30 passes through half mirrors 45 and 42, and enters the optical scan section 50.

The Stokes beam $S_T$ from the light source section 10 is reflected by a dichroic mirror 16, and divided by a half mirror 41 (corresponding to the optical splitter section) included in the optical interference section 40. The Stokes beam ($S_M$) that has passed through the half mirror 41 is used as the measurement beam (i.e., a beam applied to the subject S), and the Stokes beam ($S_S$) that has been reflected by the half mirror 41 is used as the OCT reference beam. The optical path length of the Stokes beam $S_S$ (reference beam) is adjusted by mirrors 43 and 44, passes through a half mirror 46, and enters the second optical detection section 80. The Stokes beam ($S_M$) (measurement beam) is reflected by the half mirror 42, and enters the optical scan section 50.

The pump beam P and the Stokes beam $S_M$ are adjusted to be parallel beams, and the XY plane of the subject S is scanned with the pump beam P and the Stokes beam $S_M$ via scan mirrors 52 and 54 included in the optical scan section 50. The scan mirrors 52 and 54 are controlled by the signal processing section 90. The pump beam P and the Stokes beam $S_M$ pass through a dichroic mirror 62, and condensed on the subject S through the objective lens 60. The objective lens 60 can be moved in the Z-axis direction by a driver section (not illustrated in FIG. 2) to scan the subject S in the Z-axis direction (depth direction). The driver section that drives the objective lens 60 is controlled by the signal processing section 90.

Figure 3:
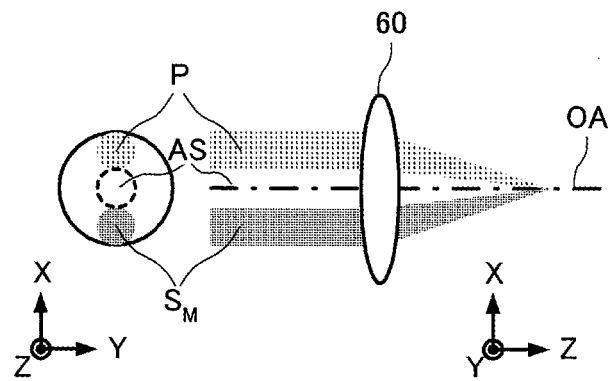
FIG. 3 is a view illustrating the positional relationship between a pump beam, a Stokes beam, and an objective lens.

The positional relationship between the pump beam P, the Stokes beam $S_M$, and the objective lens 60 is adjusted as illustrated in FIG. 3. Specifically, the optical path of the pump beam P and the optical path of the Stokes beam $S_M$ are adjusted to be symmetrical with respect to the optical axis OA of the objective lens 60. Note that the optical path of the anti-Stokes beam AS coincides with the optical axis OA.

The pump beam P and the Stokes beam $S_M$ coincide with each other at the focus position within the subject S, and an anti-Stokes beam (CARS beam) is generated due to interaction with the measurement target molecule at the focus position within the subject S. The anti-Stokes beam AS generated by the subject S is focused by the objective lens 60, is separated by the dichroic mirror 62 from the pump beam P and the Stokes beam SM, and enters the first optical detection section 70. The first optical detection section 70 is implemented by a photodiode, for example. The first optical detection section 70 receives the anti-Stokes beam AS, and outputs a detection signal to the signal processing section 90 as an anti-Stokes signal.

The Stokes beam $S_M$ that has been scattered and reflected within the subject S (reflected Stokes beam $S_M$) travels through the optical path in the opposite direction, and enters the second optical detection section 80 through the objective lens 60, the dichroic mirror 62, the optical scan section 50, and the half mirrors 42, 45, and 46 included in the optical interference section 40. The reflected Stokes beam $S_M$ interferes with the Stokes beam $S_S$ (reference beam), and is detected by the second optical detection section 80 as an interference beam. An optical path adjustment section that includes the mirrors 43 and 44 is adjusted so that the optical path length of the reflected Stokes beam $S_M$ coincides with the optical path length of the Stokes beam $S_S$ (reference beam) so that interference occurs. The second optical detection section 80 is implemented by a photodiode, for example. The second optical detection section 80 outputs an interference beam detection signal to the signal processing section 90 as an OCT interference signal.

The signal processing section 90 (computer) generates an image based on the detection signal (anti-Stokes signal) from the first optical detection section 70, and the detection signal (OCT interference signal) from the second optical detection section 80. The signal processing section 90 supplies a scan signal to the optical scan section 50 and the driver section that drives the objective lens 60 to control the scan mirrors 52 and 54 and the objective lens 60.

The signal processing section 90 performs a process that generates an image (CARS image) in which the anti-Stokes signal from the first optical detection section 70 is synchronized with the scan signal, and a process that generates an image (OCT image) in which the OCT interference signal from the second optical detection section 80 is synchronized with the scan signal. Since the scan operation with the pump beam P and the Stokes beam $S_M$ is performed in the X-Y plane and the Z-axis direction, it is possible to generate a two-dimensional image of the subject S in the X-Y plane, and a tomographic image of the subject S in the X-Z plane or the Y-Z plane. The CARS image (i.e., an image that represents molecular information) and the OCT image (i.e., an image that represents structural information) generated by the signal processing section 90 are displayed on the display section 92 (display). Note that the CARS image and the OCT image may be independently displayed on the display section 92, or an image in which the CARS image is superimposed on the OCT image (or an image in which the OCT image is superimposed on the CARS image) may be displayed on the display section 92.

Figure 4:
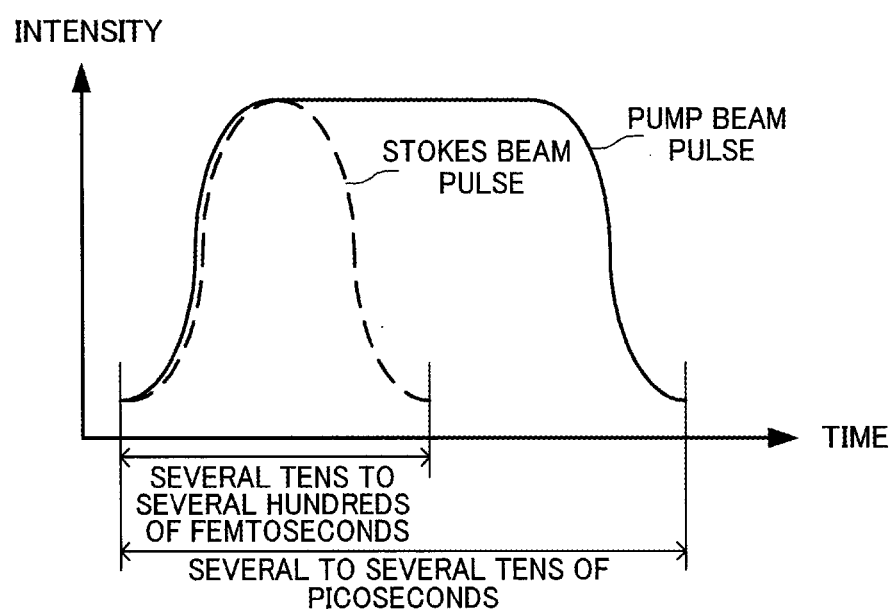
FIG. 4 is a view illustrating the pulse timing of a pump beam pulse and a Stokes beam pulse applied to a subject.

FIG. 4 illustrates the pulse timing of the pump beam pulse and the Stokes beam pulse applied to the subject S. As illustrated in FIG. 4, the Stokes beam pulse has a femtosecond pulse width (several tens to several hundreds of femtoseconds), and the pump beam pulse has a picosecond pulse width (several to several tens of picoseconds) since the pulse width of the pump beam pulse is stretched by the pulse stretch section 30. The optical path length of the pump beam is adjusted by the optical delay section 20 so that the rising edge of the Stokes beam pulse and the rising edge of the pump beam pulse almost coincide with each other.

In the CARS resonance process, the vibrational energy of the molecule is excited to the V=1 level (see FIG. 1) due to simultaneous application of the Stokes beam pulse and the pump beam pulse in the initial stage, and is further excited by application of the pump beam pulse in the subsequent stage, and the anti-Stokes beam is generated due to relaxation to the V=0 level. In the CARS non-resonance process, since the vibrational energy of the molecule is excited to the virtual level a (see FIG. 1) due to simultaneous application of the Stokes beam pulse and the pump beam pulse in the initial stage, the vibrational energy of the molecule is rarely further excited by application of the pump beam pulse in the subsequent stage, and the probability that the anti-Stokes beam is generated decreases. Specifically, the CARS signal resonance process/non-resonance process ratio (i.e., the S/N ratio of the CARS signal) can be improved by causing the rising edge of the Stokes beam pulse and the rising edge of the pump beam pulse to coincide with each other, and reducing the pulse width of the Stokes beam as compared with the pulse width of the pump beam (see FIG. 4) so that the Stokes beam is not applied in the subsequent-stage excitation process.

It is possible to avoid a mismatch in optical pulse when combining CARS and OCT by utilizing an ultrashort pulse having a pulse width of several tens to several hundreds of femtoseconds and suitable for OCT measurement as the Stokes beam, and utilizing the Stokes beam as the OCT measurement beam. This makes it possible to combine CARS and OCT.

Second Embodiment

Figure 5:
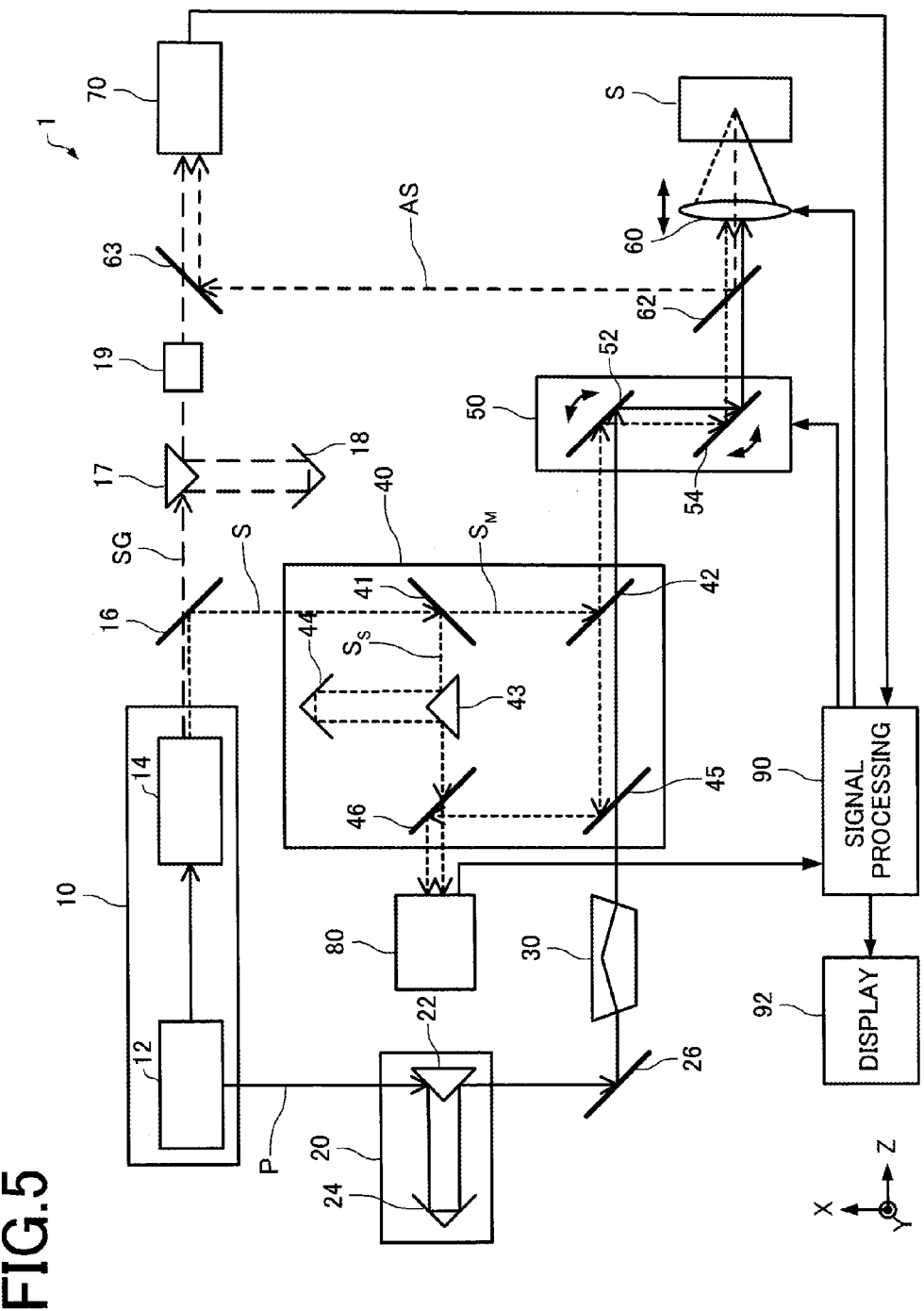
FIG. 5 is a view illustrating an example of the configuration of a measurement device according to a second embodiment.

FIG. 5 illustrates an example of the configuration of a measurement device according to a second embodiment. In FIG. 5, the same elements as those illustrated in FIG. 2 are indicated by the same reference signs, and detailed description thereof is appropriately omitted.

When the pulse width in the initial-stage CARS excitation process is set to several tens to several hundreds of femtoseconds (see FIG. 4), the population to the V=1 level decreases, and the absolute intensity of the anti-Stokes beam decreases. The measurement device 1 illustrated in FIG. 5 is configured to detect the anti-Stokes signal with high sensitivity by performing heterodyne detection using a signal beam SG from the optical parametric oscillator 14 as a reference beam.

The measurement device 1 illustrated in FIG. 5 further includes mirrors 17 and 18 that adjust the optical path length of the signal beam SG from the optical parametric oscillator 14, an optical modulation section 19 that modulates the wavelength of the signal beam SG, and a half mirror 63. The optical modulation section 19 may be implemented by an acousto-optic modulator (AOM).

The signal beam SG passes through the dichroic mirror 16, and enters the optical modulation section 19 through the mirrors 17 and 18. The signal beam SG that has been wavelength-modulated by the optical modulation section 19 passes through the half mirror 63, and enters the first optical detection section 70. The anti-Stokes beam AS from the subject S is reflected by the half mirror 63, and enters the first optical detection section 70.

Since the excitation beam of the optical parametric oscillator 14 is the second harmonic (angular frequency: $2\omega_p$) of the pump beam (angular frequency: $\omega_p$), and the angular frequency $\omega_p$ of the pump beam and the angular frequency $\omega_s$ of the Stokes beam (i.e., the idler beam of the optical parametric oscillator 14) are adjusted so that $\omega_\gamma = \omega_p - \omega_s$, the angular frequency of the anti-Stokes beam is $\omega_{as} = 2\omega_p - \omega_s$, and is equal to the angular frequency of the signal beam of the optical parametric oscillator 14.

Figure 6:
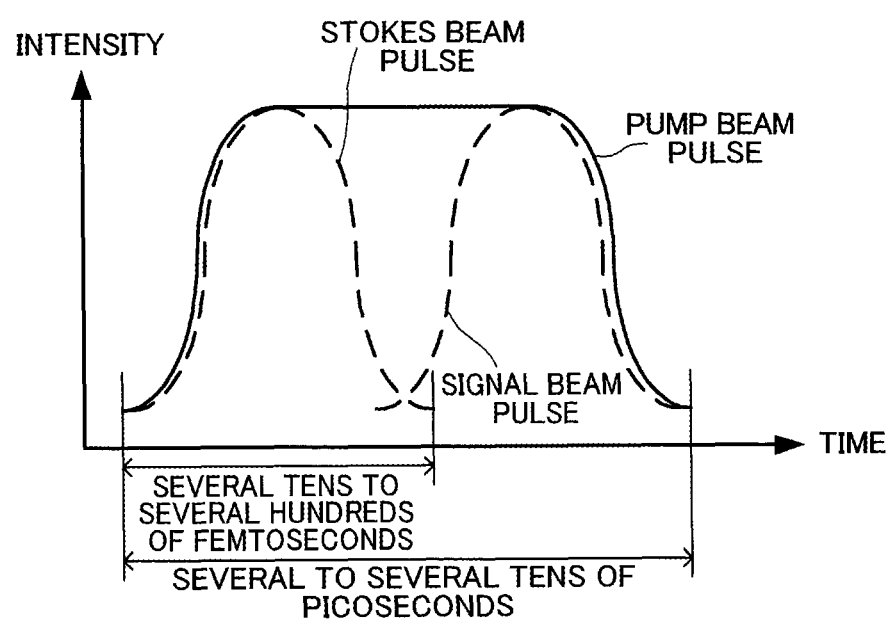
FIG. 6 is a view illustrating the pulse timing of a signal beam from an optical parametric oscillator.

Therefore, when the pulse timing of the signal beam SG is adjusted to coincide with the pulse timing of the anti-Stokes beam AS (see FIG. 6) using the mirrors 17 and 18, and the wavelength of the signal beam SG is shifted by the optical modulation section 19, the signal beam SG and the anti-Stokes beam AS interfere with each other to generate an optical beat, which is detected by the first optical detection section 70. The first optical detection section 70 outputs a beat signal of the detected optical beat to the signal processing section 90 as the anti-Stokes signal.

Note that the invention is not limited to the above embodiments, and various modifications and variations may be made of the above embodiments.

The invention claimed is:

1. A measurement device comprising:
   a light source section that generates a pump beam and a Stokes beam that are applied to a subject;
   a pulse stretch section that stretches a pulse of the pump beam so that a pulse width of the Stokes beam is shorter than a pulse width of the pump beam;
   an optical splitter section that splits the Stokes beam into two beams;
   an optical scan section that scans the subject with the pulse-stretched pump beam and one of the two beams split by the optical splitter section;
   a first optical detection section that detects an anti-Stokes beam from the subject, and outputs a detection signal;
   a second optical detection section that detects an interference beam of the other of the two beams split by the optical splitter section and the Stokes beam reflected by the subject, and outputs a detection signal; and
   a signal processing section that performs an image generation process based on the detection signal from the first optical detection section and the detection signal from the second optical detection section.

2. The measurement device as defined in claim 1,
   wherein the pulse-stretched pump beam is a picosecond pulse laser beam, and the Stokes beam is a femtosecond pulse laser beam.

3. The measurement device as defined in claim 1,
   wherein the light source section includes an optical parametric oscillator that utilizes a second harmonic of the pump beam as an excitation beam, and generates an idler beam of the optical parametric oscillator as the Stokes beam.

4. The measurement device as defined in claim 3, further comprising:
   an optical modulation section that modulates a wavelength of a signal beam from the optical parametric oscillator,
   wherein the first optical detection section detects an interference beam of the wavelength-modulated signal beam and the anti-Stokes beam from the subject, and outputs the detection signal.

5. A measurement method comprising:
   a light generation process that generates a pump beam and a Stokes beam that are applied to a subject;
   a pulse stretch process that stretches a pulse of the pump beam so that a pulse width of the Stokes beam is shorter than a pulse width of the pump beam;
   an optical split process that splits the Stokes beam into two beams;
   an optical scan process that scans the subject with the pulse-stretched pump beam and one of the two beams split by the optical split process;
   a first optical detection process that detects an anti-Stokes beam from the subject, and outputs a detection signal;
   a second optical detection process that detects an interference beam of the other of the two beams split by the optical split process and the Stokes beam reflected by the subject, and outputs a detection signal; and
   a signal processing process that performs an image generation process based on the detection signal output by the first optical detection process and the detection signal output by the second optical detection process.

6. The measurement method as defined in claim 5,
   wherein the pulse-stretched pump beam is a picosecond pulse laser beam, and the Stokes beam is a femtosecond pulse laser beam.

7. The measurement method as defined in claim 5,
   wherein the light generation process generates an idler beam of an optical parametric oscillator as the Stokes beam, the optical parametric oscillator utilizing a second harmonic of the pump beam as an excitation beam.

8. The measurement method as defined in claim 7, further comprising:
   an optical modulation process that modulates a wavelength of a signal beam from the optical parametric oscillator,
   wherein the first optical detection process detects an interference beam of the wavelength-modulated signal beam and the anti-Stokes beam from the subject, and outputs the detection signal.

9. The measurement device as defined in claim 2,
   wherein the light source section includes an optical parametric oscillator that utilizes a second harmonic of the pump beam as an excitation beam, and generates an idler beam of the optical parametric oscillator as the Stokes beam.

10. The measurement device as defined in claim 9, further comprising:
    an optical modulation section that modulates a wavelength of a signal beam from the optical parametric oscillator,
    wherein the first optical detection section detects an interference beam of the wavelength-modulated signal beam and the anti-Stokes beam from the subject, and outputs the detection signal.

11. The measurement method as defined in claim 6,
    wherein the light generation process generates an idler beam of an optical parametric oscillator as the Stokes beam, the optical parametric oscillator utilizing a second harmonic of the pump beam as an excitation beam.

12. The measurement method as defined in claim 11, further comprising:
    an optical modulation process that modulates a wavelength of a signal beam from the optical parametric oscillator,
    wherein the first optical detection process detects an interference beam of the wavelength-modulated signal beam and the anti-Stokes beam from the subject, and outputs the detection signal.

* * * * *